United States Patent

Blankenburg et al.

[11] Patent Number: 6,153,179
[45] Date of Patent: Nov. 28, 2000

[54] HAIR SETTING LOTIONS

[75] Inventors: Rainer Blankenburg, Ludwigshafen; Karin Sperling, Neustadt; Axel Sanner, Frankenthal, all of Germany

[73] Assignee: BASF Aktiengesellschaft, Ludwigshafen, Germany

[21] Appl. No.: 08/879,775

[22] Filed: Jun. 20, 1997

Related U.S. Application Data

[63] Continuation of application No. 08/620,298, Mar. 22, 1996, abandoned.

[30] Foreign Application Priority Data

Mar. 27, 1995 [DE] Germany .................. 195 10 474

[51] Int. Cl.$^7$ ..................................... A61K 7/11
[52] U.S. Cl. ....................... 424/70.11; 424/70.14; 424/70.15; 424/70.16; 424/70.17
[58] Field of Search ............. 424/70.15, 70.14, 424/70.16, 70.17, 70.11

[56] References Cited

U.S. PATENT DOCUMENTS

| | | | |
|---|---|---|---|
| 3,145,147 | 8/1964 | Glickman | 424/70.17 |
| 4,521,404 | 6/1985 | Lorenz et al. | 424/71 |
| 4,923,694 | 5/1990 | Shih et al. | 424/70 |
| 5,182,098 | 1/1993 | Kopolow et al. | 424/47 |
| 5,221,531 | 6/1993 | Kopolow et al. | 424/71 |
| 5,603,919 | 2/1997 | Liu et al. | 424/47 |
| 5,637,296 | 6/1997 | Rocafort | 424/70.11 |
| 5,660,816 | 8/1997 | Adams et al. | 424/45 |
| 5,716,634 | 2/1998 | Tseng et al. | 424/445 |

FOREIGN PATENT DOCUMENTS

| | | |
|---|---|---|
| 74 191 | 3/1983 | European Pat. Off. . |
| 219830 | 4/1987 | European Pat. Off. . |
| 455 081 | 11/1991 | European Pat. Off. . |
| 635257 | 1/1995 | European Pat. Off. . |
| 4013873 | 10/1991 | Germany . |
| WO93/17658 | 9/1993 | WIPO . |

*Primary Examiner*—David W. Wu
*Assistant Examiner*—Caixia Lu
*Attorney, Agent, or Firm*—Keil & Weinkauf

[57] ABSTRACT

Hair setting lotion which are not subject to hydrolysis and which are made up of A) 0.5–20% by weight of a nonionic or anionic homo- or copolymer of at least 70% by weight of N-vinylcaprolactam (polymer A), and B) 0.5–20% by weight of a further film-forming polymer (polymer B), selected from the group consisting of polyamides, polyurethanes, and homo- and copolymers of monoolefinically unsaturated monomers.

5 Claims, No Drawings

HAIR SETTING LOTIONS

This application is a continuation of application Ser. No. 08/620,298, filed on Mar. 22, 1996 now abandoned.

The present invention relates to novel hair setting lotions which comprise polymer mixtures as film formers.

Hairspray compositions which comprise a polyester and a water-soluble polymer, for example a copolymer of N-vinylcaprolactam and N-vinylpyrrolidone, are disclosed in WO 93/17658.

Such hairsprays, however, are sensitive to hydrolysis and therefore can only be used and handled in a restricted manner.

It is an object of the present invention to develop hair setting lotions which have good setting properties combined with good washing-out ability and low stickiness without showing the sensitivity to hydrolysis described above.

We have found that this object is achieved by hair setting lotions comprising:

A) 0.5–20% by weight of a homo- or copolymer of at least 70% by weight of N-vinylcaprolactam (polymer A), and B) 0.5–20% by weight of a further film-forming polymer (polymer B), selected from the group consisting of polyamides, polyurethanes, and homo- and copolymers of monoolefinically unsaturated monomers.

Suitable polymers A are homopolymers of N-vinylcaprolactam, which are known to the person skilled in the art and can be prepared, for example, by the procedure described in U.S. Pat. No. 3,145,147.

Further suitable polymers A are copolymers of N-vinylcaprolactam and further polymerizable monomers, the copolymers comprising at least 70% by weight, preferably at least 85% by weight, of N-vinylcaprolactam.

Suitable further polymerizable monomers for the copolymers A are:

monomers having an acid function, such as acrylic acid, methacrylic acid, acrylamidomethylpropylsulfonic acid (AMPS), 3-sulfopropyl (meth)acrylate, if desired also in completely or partially neutralized form;

$C_1$–$C_{18}$ alkyl (meth)acrylates, such as tert-butyl acrylate, ethyl acrylate, isobutyl methacrylate, n-butyl methacrylate, methyl methacrylate, ethyl methacrylate and hydroxyalkyl (meth)acrylic acid esters;

vinyl esters of $C_2$–$C_{10}$ fatty acids such as vinyl acetate, vinyl propionate and vinyl esters of relatively long-chain and/or branched fatty acids, for example versatic acid;

$C_3$–$C_8$ N-alkyl(meth)acrylamides, such as methacrylamide, N,N-dimethylacrylamide, N-tert-butylacrylamide and N-tert-octylacrylamide;

N-vinylpyrrolidone and N-vinylpiperidone.

The other monomers can be used for the copolymer A as an individual compound or as a mixture.

Such copolymers are known or can be prepared by customary polymerization processes.

For example, EP 455081 describes copolymers of N-vinylpyrrolidone, N-vinylcaprolactam and N-vinylimidazole. EP 74191 discloses copolymers of N-vinylpyrrolidone, N-vinylcaprolactam and dimethylaminoethyl methacrylate.

Homopolymers of N-vinylcaprolactam are preferably used for the hair setting lotions according to the invention.

The hair setting lotions according to the invention comprise the polymers A in an amount of 0.5–20, preferably of 1–10%, by weight based on the finished lotion.

As polymers B, a multiplicity of polymers used in hair cosmetics can be employed.

Suitable polymers B) are further film-forming polymers other than A) according to the invention, selected from the group consisting of polyamides, polyurethanes and homo- and copolymers of monoolefinically unsaturated monomers. Film-forming polymers can be customary hair setting polymers according to the invention, but also film formers for industrial coating agents and binders.

Suitable homo- and copolymers of monoolefinically unsaturated monomers are especially homo- and copolymers of $C_1$–$C_{12}$-alkyl acrylates and methacrylates, monoolefinically unsaturated $C_3$–$C_5$-monocarboxylic acids and their vinyl esters, maleic acid and its hemiesters, methyl vinyl ether, acrylamides, methacrylamides, N-alkyl-substituted (meth)acrylamides, N-vinylpyrrolidone, N-vinylimidazole and styrene.

Particularly preferred polymers B) are acrylate polymers, such as copolymers of acrylic acid/ethyl acrylate/N-tertiary butyl-acrylamide, copolymers of methacrylic acid/tertiary butyl acrylate/N-vinylpyrrolidone, copolymers based on acrylic acid and vinyl acetate, copolymers of octylacrylamide/acrylate/ butylaminoethyl methacrylate, copolymers of octylacrylamide/ acrylate, copolymers of ethyl methacrylate/methacrylic acid/ N-vinylpyrrolidone or copolymers of acrylate and hydroxyalkyl acrylate. Such copolymers are marketed, for example, under the trade names Amerhold®, Ultraholde® 8, Ultrahold Strong®, Luviflex® VBM, Luvimer® 100P, Luvimer® 36D, Luvimer® MAE30D, Acronal® 500D, Acudyne®255, Stepanhold®, Lovocryle® Versatyl® and Amphomer®.

Preferred polymers B are sulfonate-bearing polyamides, comprising:

from 20 to 99 mol % of a monoaminocarboxylic acid having 2 to 12 C atoms or its lactam, from 0.5 to 40 mol % of a diamine having 2 to 18 C atoms, from 0.5 to 25 mol % of a sulfonate-bearing dicarboxylic acid having 4 to 12 C atoms, and from 0 to 35 mol % of a further dicarboxylic acid having 2 to 16 C atoms.

Preferred polymers B) are furthermore sulfonate-bearing acrylates comprising:

from 50 to 90% by weight of one or more monomers from the group consisting of $C_1$–$C_{18}$-alkyl esters of acrylic acid or of methacrylic acid and vinyl esters of saturated $C_2$–$C_{10}$-monocarboxylic acids, from 10 to 25% by weight of a sulfonic acid-bearing vinyl monomer, and from 0 to 40% by weight of a further monomer from the group consisting of acrylic acid, methacrylic acid, acrylamide, methacrylamide, $C_3$–$C_8$-N-alkylacrylamide and N,N-dimethylacrylamide.

Likewise preferred polymers B) are copolymers in the form of microdispersions according to DE-A 43 27 514, which are obtainable by free radical-initiated copolymerization or by the use of ionizing radiation-initiated copolymerization of:

from 40 to 99% by weight of one or more water-insoluble, monoethylenically unsaturated monomers, from 1 to 60% by weight of one or more water-soluble, monoethylenically unsaturated monomers and from 0 to 30% by weight of one or more polyethylenically unsaturated monomers in aqueous medium in the presence of from 2 to 20% by weight, based on the total amount of the monomers, of surface-active compounds as emulsifiers, having a mean particle size of from 5 to 37 nm, determined by light scattering in aqueous medium.

Suitable polymers B) are also homo- and copolymers of N-vinylpyrrolidone, such as are marketed, for example, by BASF Aktiengesellschaft under the name Luviskol®. The copolymers are obtainable by polymerization of N-vinylpyrrolidone with vinyl acetate and/or vinyl propionate in various weight ratios. Examples of such polymers are:

Luviskol® K17, Luviskol® K30, Luviskol® K60, Luviskole® K80, Luviskol® K90 (polyvinylpyrrolidones of appropriate K value as a powder or as a solution (aqueous or aqueous/alcoholic)).

Luviskol® VA=vinylpyrrolidone/vinyl acetate copolymers, in particular Luviskol® VA 73, Luviskol® VA 64, Luviskole® VA 55, Luviskol® VA 37 and Luviskol® VA 28.

Other suitable polymers B are ternary polymers of vinylpyrrolidone, vinyl acetate and vinyl propionate, for example Luviskole® VAP 343.

Likewise suitable are vinyl acetate copolymers with crotonic acid, for example the products Luviset® CA, Luviset® CAP and National® 28-2930.

Quaternized polyquaternium-4, polyquaternium-6, polyquaternium-7, polyquaternium-10, polyquaternium-11 or polyquaternium 16 can also be used.

Other suitable polymers B) are copolymers of methyl vinyl ether (MVE) and maleates, for example copolymers of MVE/monoethyl maleate, MVE/monoisopropyl maleate or MVE/monobutyl maleate, for example the products Gantrez ES-225, Gantrez® ES-335, Gantrez® ES-425, Gantrez® ES-435 and Gantrez® SP-215.

Polyurethanes, as are disclosed, for example, in WO 94/03510, can also be employed as polymer B. Likewise suitable are sodium salts of polystyrenesulfonic acid such as are marketed under the name Flexan® 130.

If they are synthesized from acid-bearing monomers, the polymers A and B can be used in the acid form or in partially or completely neutralized form for the hair setting lotions according to the invention. Alkali metal hydroxides, ammonia and organic amines, in particular aminoalcohols, are suitable for the neutralization, 2-amino-2-methyl-1-propanol being very particularly preferred.

The polymers A and B are present in a solvent, the solvent employed preferably being water or alcohols or mixtures of water and lower alcohols. The proportion of solvent in the hair setting lotion is customarily 25–98% by weight.

The polymers A and B can be mixed together by dissolving A and B in a solvent as a powder, or by admixing, to a solution of one polymer, the other polymer in each case as a solid or, likewise, as a solution. Polymer B can also be present as a dispersion, it being possible for polymer A to be added as a powder or aqueous or aqueous-alcoholic solution.

The hair setting lotions according to the invention contain the polymers B in an amount of 0.5–20.0, preferably of 1–5%, by weight based on the finished lotion.

In addition to the polymers A and B and a solvent, the hair setting lotions according to the invention, depending on the intended use, can contain further customary hair cosmetic additives such as perfume oils, emulsifiers, preservatives, maintenance substances such as panthenol, collagen, vitamins, protein hydrolyzates, stabilizers, pH regulators, colorants and other customary additives.

If the hair setting lotion according to the invention is to be used as a hairspray, as a rule a propellant is added. Customary propellants are lower alkanes, for example propane or butane, dimethyl ether, nitrogen, nitrous oxide or carbon dioxide or mixtures of these substances. The hair setting lotions according to the invention can also contain halogen-containing hydrocarbons as propellants. When using in mechanical spray devices, for example spray pumps, the propellant can be dispensed with.

The hair setting lotions according to the invention have outstanding application properties; they form clear films and in aqueous/alcoholic solutions have a low solution viscosity, so that they also still have good spray properties in more highly concentrated form. Surprisingly, water-insoluble film-forming polymers can also be processed in combination with polyvinylcaprolactams to give hair setting lotions which can readily be washed out.

The polyvinylcaprolactam solutions used in the examples below were 50% strength by weight solutions in ethanol. The K value according to Fikentscher of the polymer was 40 (1% in ethanol).

EXAMPLE 1

Preparation and properties of a hair setting lotion

| | |
|---|---|
| 4.0% by weight | of Luvimer ® 36D (36% strength by weight aqueous dispersion of a copolymer of tert-butyl acrylate, ethyl acrylate and methacrylic acid) |
| 7.0% by weight | of polyvinylcaprolactam solution |
| 89.0% by weight | of dist. water |

+) K value 40 were dissolved at room temperature and filled into a spray pump. After spraying two model heads, the following assessment of the lotion resulted:

The treated hair had a good set combined with a good sheen without the hair being sticky. The hold is soft, and the combability and the washing-out ability are good.

EXAMPLES 2 TO 9

The appearance and properties of treated strands of hair and the stickiness of formulations of the compositions mentioned below were determined. The results are listed in the table.

The strands of hair were dipped in the respective formulations, lightly squeezed off on filter paper, dried and their stiffness was examined.

The wasting-out ability was determined by washing the hair strands treated as above in a 10% strength by weight aqueous sodium lauryl ether sulfate solution at 37° C. for 30 sec by immersing five times and squeezing out. The strands of hair were then rinsed with clear water, the washing-out process was repeated and the strands of hair were squeezed out on filter paper and dried overnight. The hair was then examined for residues.

Assessment of the stickiness

The formulations were spread on a glass sheet using a doctor blade having a 120 $\mu$m gap width. The wet film was dried at room temperature and then stored overnight at 75% relative atmospheric humidity and 20° C. in an air-conditioned cabinet. For testing, a plastic-carbon tape was pressed onto the polymer film with a round rubber stamp ($\phi$ 40 mm, Shore A hardness 60±5) at 250N for 10 sec. The printing ink of the carbon tape remains adhering to the polymer film to the extent to which the polymer surface is sticky. A stickiness of 1 means that the printing ink only remains adhering to the polymer film to an extremely small extent.

EXAMPLE 2

| | |
|---|---|
| 5% by weight | of polyvinylcaprolactam solution |
| 10.0% by weight | of polyurethane according to Example 3, WO 94/03510 as a 25% strength by weight aqueous microdispersion |
| 85.0% by weight | of dist. water |

EXAMPLE 3

| | |
|---|---|
| 5% by weight | of polyvinylcaprolactam solution |
| 2.5% by weight | of polyamide from 20 mol % $\epsilon$-caprolactam, 34 mol % hexamethylenediamine, 17 mol % 5-sulfoisophthalic acid sodium salt and 17 mol % isophthalic acid |
| 92.5% by weight | of dist. water |

EXAMPLE 4

| | |
|---|---|
| 5% by weight | of polyvinylcaprolactam |
| 10% by weight | of acrylate microdispersion according to Example 10, DE-A 43 27 514 (solids content 20% by weight) |
| 85% by weight | of dist. water |

EXAMPLE 5

| | |
|---|---|
| 5.0% by weight | of polyvinylcaprolactam solution |
| 2.5% by weight | of Luviskol VA 64P, powdered copolymer of N-vinylpyrrolidone/vinyl acetate |
| 52.5% by weight | of abs. ethanol |
| 40.0% by weight | of dist. water |

EXAMPLE 6

| | |
|---|---|
| 5% by weight | of polyvinylcaprolactam solution |
| 2.5% by weight | of Luvimer 100P, powder of a copolymer of tertiary butyl acrylate/ethyl acrylate/methacrylic acid |
| 0.58% by weight | of 2-amino-2-methylpropanol (AMP) |
| 52.50% by weight | of abs. ethanol |
| 39.42% by weight | of dist. water |

EXAMPLE 7

| | |
|---|---|
| 5% by weight | of polyvinylcaprolactam solution |
| 2.5% by weight | of Luviset CAP, powdered terpolymer of vinyl acetate/vinyl propionate/crotonic acid |
| 0.19% by weight | of AMP |
| 52.50% by weight | of abs. ethanol |
| 39.81% by weight | of dist. water |

EXAMPLE 8

| | |
|---|---|
| 5% by weight | of polyvinylcaprolactam solution |
| 2.5% by weight | of Ultrahold 8, powdered terpolymer of N-tertiary butylacrylamide, ethyl acrylate and acrylic acid |
| 0.23% by weight | of AMP |
| 52.50% by weight | of abs. ethanol |
| 39.77% by weight | of dist. water |

EXAMPLE 9

| | |
|---|---|
| 5% by weight | of polyvinylcaprolactam solution |
| 2.5% by weight | of Amphomer, alkylacrylamide/acrylate copolymer |
| 0.41% by weight | of AMP |
| 52.50% by weight | of abs. ethanol |
| 39.59% by weight | of dist. water |

EXAMPLE 10

| | |
|---|---|
| 6.8% by weight | of polyvinylcaprolactam solution |
| 3.4% by weight | of Acronal 500D, 50% strength by weight aqueous anionic copolymer dispersion of an acrylate/vinyl acetate copolymer |
| 89.8% by weight | of dist. water |

TABLE

| Ex. No. | Appearance Solution | Hair strand Film on a glass sheet | Treated stiffening effect | washing-out ability | Stickiness of 5% strength by weight solution, at 20° C. and 80% rel. humidity |
|---|---|---|---|---|---|
| 2 | clear | clear | very good | good | 1 |
| 3 | clear | clear | very good | good | 1 |
| 4 | opaque | clear | very good | good | 1 |
| 5 | clear | clear | very good | good | 1 |
| 6 | clear | clear | very good | good | 1 |
| 7 | clear | clear | very good | good | 1 |
| 8 | clear | clear | very good | good | 1 |
| 9 | clear | almost clear | very good | good | 1 |
| 10 | milky | almost clear | very good | still good | 1 |

EXAMPLE 11

5% by weight of polyvinylcaprolactam solution 2.5% by weight of Luvimer 100 P 0.58% by weight of AMP 52.50% by weight of ethanol 39.42% by weight of a 50:50 mixture of propane and butane

EXAMPLE 12

5% by weight of polyvinylcaprolactam 2.5% by weight of Ultrahold 8 solution 2.5% by weight of AMP 37.27% by weight of ethanol 60% weight of a 30:50:20 mixture of propane, butane and n-pentane.

What is claimed is:

1. A hair setting lotion comprising:
   A) 0.5–20% by weight based on the weight of the finished lotion of a homopolymer of N-vinylcaprolactam,
   B) 0.5–20% by weight based on the weight of the finished lotion of a further film-forming polymer (polymer B), selected from the group consisting of
      an acrylate copolymer comprising as a monomer N-tertiary butylacrylamide or octacrylamide,
      a polyurethane,
      a vinyl acetate copolymer with crotonic acid, and
      a copolymer of methyl vinyl ether and a maleate.

2. A hair setting lotion as defined in claim 1, wherein the polymer B is an acrylate copolymer comprising as a monomer N-tertiary butylacrylamide or octacrylamide.

3. A hair setting lotion as defined in claim 1, wherein the polymer B is a polyurethane.

4. A hair setting lotion as defined in claim 1, wherein the polymer B is a vinyl acetate copolymer with crotonic acid.

5. A hair setting lotion as defined in claim 1, wherein the polymer B is a copolymer of methyl vinyl ether and a maleate.

* * * * *